US007985892B1

(12) United States Patent
Gao et al.

(10) Patent No.: US 7,985,892 B1
(45) Date of Patent: Jul. 26, 2011

(54) TRUNCATED CRY35 PROTEINS

(75) Inventors: Yong Gao, Westfield, IN (US); Rod Aaron Herman, New Ross, IN (US); Andrew William Carr, Beech Grove, IN (US); Deborah Ann Schwedler, Greenwood, IN (US); Xioaping Xu, Westfield, IN (US); George Erwin Schwab, Encinitas, CA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 11/168,194

(22) Filed: Jun. 28, 2005

Related U.S. Application Data

(60) Provisional application No. 60/584,324, filed on Jun. 29, 2004.

(51) Int. Cl.
*A01H 5/00* (2006.01)
*C12N 15/32* (2006.01)
*C12N 15/09* (2006.01)

(52) U.S. Cl. ..................... 800/302; 536/23.71; 424/93.2

(58) Field of Classification Search ........................ None
See application file for complete search history.

(56) References Cited

U.S. PATENT DOCUMENTS 5,605,793 A 2/1997 Stemmer
6,677,148 B1 1/2004 Narva et al.

FOREIGN PATENT DOCUMENTS

WO WO 97/40162 A2 10/1997
WO WO 00/24904 A1 5/2000
WO WO 00/66742 A2 11/2000
WO WO 01/14417 A2 3/2001

OTHER PUBLICATIONS

Moellenbeck et al (2001, Nature Biotechnol. 19:668-672).*
Guo et al (2004, Proc. Natl. Acad. Sci. USA 101: 9205-9210).*
Baum et al, 2004, Appl. Environ. Microbiol. 70:4889-4898.*
Ellis et al (2002, Appl. Environ. Microbiol. 68:1137-1145).*
Patterson et al, 1995, Anal. Chem. 67:3971-3978.*
Clark et al (1990, J. Bacteriol. 172:6759-6763).*
Chaurand et al (1998, J. Am. Soc. Mass. Spectrom. 10:91-103).*
de Maagd et al, 2001, Trends Genet. 17: 193-199.*
Altschul, S.F. et al. "Gapped BLAST and PSI-BLAST: A New Generation of Protein Database Search Programs" *Nucleic Acids Research*, 1997, pp. 3389-3402, vol. 25, No. 17.
Ellis, R.T. "Novel *Bacillus thuringiensis* Binary Insecticidal Crystal Proteins Active on WEstern Corn Rootworm, *Diabrotica virgifera virgifera* LeConte" *Applied and Environmental Microbiology*, Mar. 2002, pp. 1137-1145, vol. 68, No. 3.
Herman, R.A. et al. "Binary Insecticidal Crystal Protein from *Bacillus thuringiensis*, Strain PS149B1: Effects of Individual Protein Components and Mixtures in Laboratory Bioassays" *Journal of Economic Entomology*, 2002, pp. 635-639, vol. 95, No. 3.
Hofte, H. and Whiteley, H.R. "Insecticidal Crystal Proteins of *Bacillus thuringiensis*" *Microbiological Reviews*, Jun. 1989, pp. 242-255, vol. 53, No. 2.
Karlin, S. and Altschul, S.F. "Applications and Statistics for Multiple High-Scoring Segments in Molecular Sequences" *Proc. Natl. Acad.*, Jun. 1993, pp. 5873-5877, vol. 90.
Karlin, S. and Altschul, S.F. "Methods for Assessing the Statistical Significance of Molecular Sequence Features by Using General Scoring Schemes" *Proc. Natl. Acad. Sci.*, Mar. 1990, pp. 2264-2268, vol. 87.
Crickmore et al. *Bacillus thuringiensis* Toxin Nomenclature Official Website, Full Toxin List, Cry35 proteins (Aug. 2, 2005).
NCBI Accession No. AAG41672; Publication Date: Sep. 26, 2002.
NCBI Accession No. AAG50117; Publication Date: Mar. 4, 2002.
NCBI Accession No. AAG50342; Publication Date: Mar. 4, 2002.
NCBI Accession No. AAK64561; Publication Date: Jul. 29, 2004.
NCBI Accession No. AAK64563; Publication Date: Jul. 29, 2004.
NCBI Accession No. AAK64566; Publication Date: Jul. 29, 2004.

* cited by examiner

*Primary Examiner* — Anne Kubelik
(74) *Attorney, Agent, or Firm* — Ronald S. Maciak; Baker & Daniels LLP

(57) ABSTRACT

This invention provides truncated Cry35 proteins that surprisingly and unexpectedly have increased pesticidal activity as compared to full-length Cry35 proteins. The subject invention also includes polynucleotides that encode these truncated proteins, transgenic plants comprising a truncated gene of the subject invention, and transgenic plants that produce these truncated proteins. This invention further provides methods of controlling plant pests, including rootworms, with these truncated proteins. The truncated Cry35 proteins of the subject invention are preferably used in combination with Cry34 proteins, which are known in the art. Various surprising advantages of the subject invention will be apparent in light of this disclosure.

11 Claims, 1 Drawing Sheet

```
PS149B1-44    1 MLDTNKVYEISNHANGLYAATYLSEDDSGVSLMKNDDIDDYNLKWLFLPIDDQYIITSY  62
PS167H2-44    1 MLDTNKIYEISNYANGLHAATYLSEDDSGVSLMKNDDIDDYNLRWLFLPIDDQYIITSY  62
PS80JJ1-44    1 MLDTNKVYEISNLANGLYTSTYLSEDDSGVSLMSKKEDIDDYNLKWLFLPIDNNQYIITSY 62
PS201L3-44    1 MIETNKIYEISNKANGLYATTYLSEDNSGVSLENKNESDINDYNLKFLFPIDNNQYIITSY 62

PS149B1-44   63 ANNCKVWNVNNDKINVSTYSSTNSIQKWQIKANGSSYVIQSDNGKVLTAGTGQAIGLIRLT 124
PS167H2-44   63 AANNCKVWNVNNDKINVSTYSSTNSIQKWQIKANASSYVIQNNGKVLTAGTGQSIGLIRLT 124
PS80JJ1-44   63 GANNCKVWNVNKDKINVSTYSSTNSVQKWQIKAKDSSYIIQSDNGKVLTAGVGQSIGTVRLT 124
PS201L3-44   63 GVNKNKVWTANGNKINVITYSAENSAQQWQIRNSSSGYIIENNNGKILTAGTGQSIGLYLI 124

PS149B1-44  125 DESSNNPNQQWNLTSVQTIQLPQKPIIDTKLKDYPKYSPTGNID-NGTSPQLMGWTLVPCIM 185
PS167H2-44  125 DESPDNPNQQWNLTPVQTIQLPKPTIDTKLKDYPKYSQTGNID-KGTPQLMGWTLIPCIM 185
PS80JJ1-44  125 DEFPENSNQQWNLTPVQTIQLPQKPKIDEKLKDHPEYSETGNIN-PKITPLMGWTLVPCIM 185
PS201L3-44  125 DEIPEDSNQQWNLTSLQTISLPSQPIIDTTLVDYPKYSTTGSINYNGTALQLMGWTLIPCIM 186

PS149B1-44  186 VNDPNIDK-NTQIKTTPYYIEKKYQYWQRAVGSNVAIREHEKKSYTYEWGTEIDQKTTINT 246
PS167H2-44  186 VNDPNIDK-NTQIKTTPYYIEKKYQYWQQAVGSNVAIREHEKKSYAYEWGTEIDQKTTINT 246
PS80JJ1-44  186 VNDSKIDK-NTQIKTTPYYIEKKYKYWNLAKGSNVSLLPHQKRSYDYEWGTEKNQKTTINT 246
PS201L3-44  187 VMDKTIASTHTQITTTPYYILKKYQRWVLATGSGLSVPAHVKSHFEYEWGTDTDQKTSVINT 248

PS149B1-44  247 LGFQINIDSGMKFDIPEVGGGTDEIKTQLNEELKIEYSHETKIMEKYQEQSEIDNE-IDQSM 307
PS167H2-44  247 LGFQINIDSGMKFDIPEVGGGTDEIKTQLNEELKIEYSRETKIMEKYQEQSEIDNE-IDQSM 307
PS80JJ1-44  247 VGLQINIDSGMKFEVPEVGGGTEDIKTQLTEELKVEYSTETKIMTKYQEHSEIDNE-INQPM 307
PS201L3-44  249 LGFQINTDKLKATVPEVGGGTTDEIRTQTEELKWEYSSENKEMRKYKQSFDVDNINDEAL 310

PS149B1-44  308 NSIGFLTITSLELYRYNGSEIRIMQIQTSDNDTYNVTSYPNHQQALLLTNHSYEEVEEITN 369
PS167H2-44  308 NSIGFLTITSLELYRYNGSEISVMKIQTSDNDTYNVTSYPDHQQALLLTNHSYEEVEEITN 369
PS80JJ1-44  308 NSIGLHIYTSLELYRYNGHEIKIMDIETSDHDTYHLTPYPNHKEALLLTNHSYEEVEEITK 369
PS201L3-44  311 NAVGFIVETSELYRMNGN-VLITSIKTHNKDTYNTVLYPNHKEVLLLLTNHSYEEVTALTG 371

PS149B1-44  370 IPKSTLKKLKKYYF    383  (SEQ ID NO:3)
PS167H2-44  370 IPKISLKKLKKYYF    383  (SEQ ID NO:6)
PS80JJ1-44  370 IPKHTLIKLKKHYFKK  385  (SEQ ID NO:1)
PS201L3-44  372 ISKERLQNLKNNWKKR  387  (SEQ ID NO:7)
```

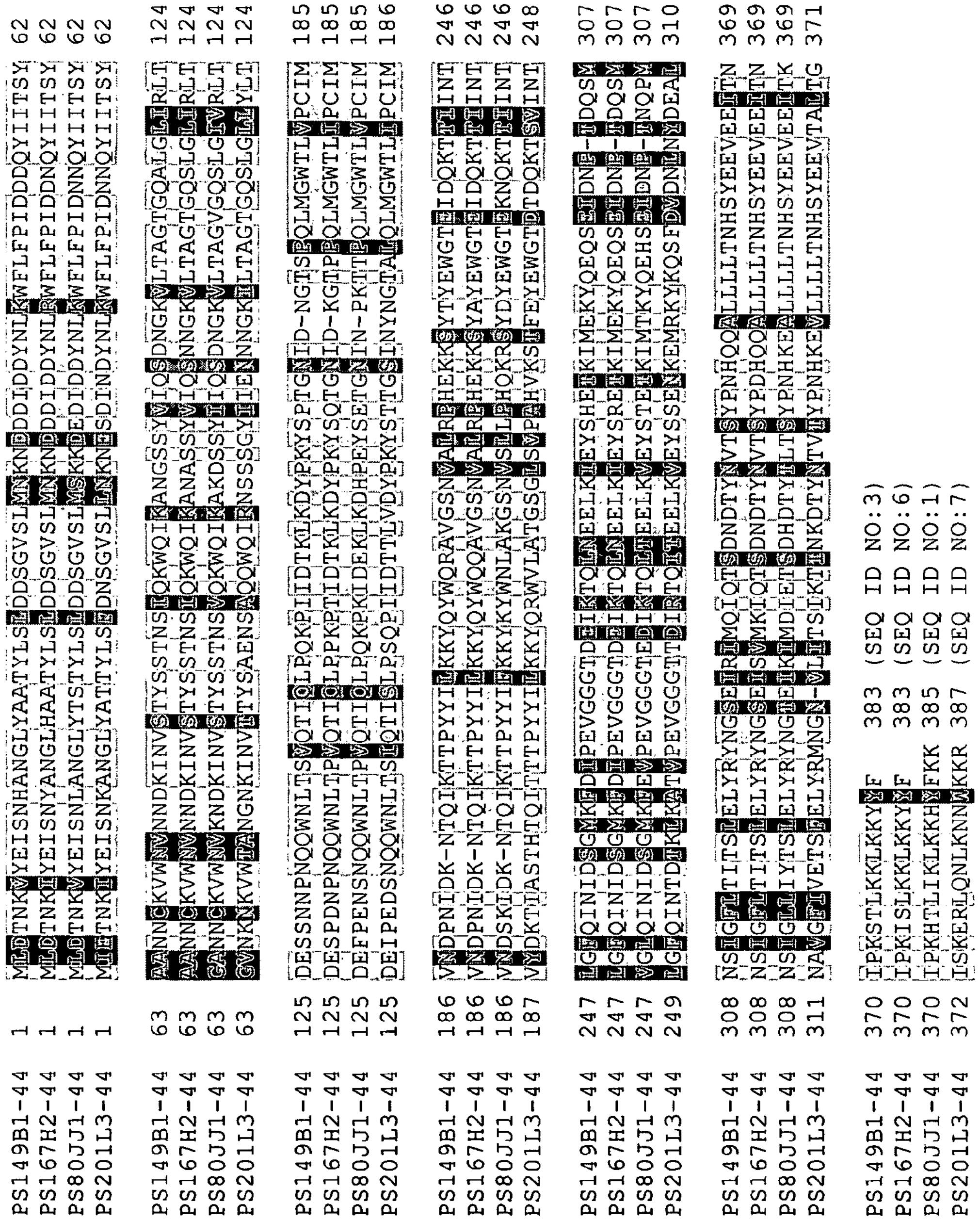

Fig. 1

SEQUENCE LISTING

```
<160> NUMBER OF SEQ ID NOS: 7

<210> SEQ ID NO 1
<211> LENGTH: 385
<212> TYPE: PRT
<213> ORGANISM: Bacillus thuringiensis

<400> SEQUENCE: 1

Met Leu Asp Thr Asn Lys Val Tyr Glu Ile Ser Asn Leu Ala Asn Gly
1               5                   10                  15

Leu Tyr Thr Ser Thr Tyr Leu Ser Leu Asp Asp Ser Gly Val Ser Leu
            20                  25                  30

Met Ser Lys Lys Asp Glu Asp Ile Asp Asp Tyr Asn Leu Lys Trp Phe
        35                  40                  45

Leu Phe Pro Ile Asp Asn Asn Gln Tyr Ile Ile Thr Ser Tyr Gly Ala
    50                  55                  60

Asn Asn Cys Lys Val Trp Asn Val Lys Asn Asp Lys Ile Asn Val Ser
65                  70                  75                  80

Thr Tyr Ser Ser Thr Asn Ser Val Gln Lys Trp Gln Ile Lys Ala Lys
                85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335
```

```
Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385


<210> SEQ ID NO 2
<211> LENGTH: 354
<212> TYPE: PRT
<213> ORGANISM: Bacillus thuringiensis

<400> SEQUENCE: 2

Met Leu Asp Thr Asn Lys Val Tyr Glu Ile Ser Asn Leu Ala Asn Gly
1               5                   10                  15

Leu Tyr Thr Ser Thr Tyr Leu Ser Leu Asp Asp Ser Gly Val Ser Leu
            20                  25                  30

Met Ser Lys Lys Asp Glu Asp Ile Asp Asp Tyr Asn Leu Lys Trp Phe
        35                  40                  45

Leu Phe Pro Ile Asp Asn Asn Gln Tyr Ile Ile Thr Ser Tyr Gly Ala
    50                  55                  60

Asn Asn Cys Lys Val Trp Asn Val Lys Asn Asp Lys Ile Asn Val Ser
65                  70                  75                  80

Thr Tyr Ser Ser Thr Asn Ser Val Gln Lys Trp Gln Ile Lys Ala Lys
                85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320
```

```
Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu


<210> SEQ ID NO 3
<211> LENGTH: 383
<212> TYPE: PRT
<213> ORGANISM: Bacillus thuringiensis

<400> SEQUENCE: 3

Met Leu Asp Thr Asn Lys Val Tyr Glu Ile Ser Asn His Ala Asn Gly
1               5                   10                  15

Leu Tyr Ala Ala Thr Tyr Leu Ser Leu Asp Asp Ser Gly Val Ser Leu
            20                  25                  30

Met Asn Lys Asn Asp Asp Asp Ile Asp Asp Tyr Asn Leu Lys Trp Phe
        35                  40                  45

Leu Phe Pro Ile Asp Asp Asp Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser His Glu Thr Lys
        275                 280                 285

Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335
```

-continued

Asp Asn Asp Thr Tyr Asn Val Thr Ser Tyr Pro Asn His Gln Gln Ala
340 345 350

Leu Leu Leu Leu Thr Asn His Ser Tyr Glu Glu Val Glu Glu Ile Thr
355 360 365

Asn Ile Pro Lys Ser Thr Leu Lys Lys Leu Lys Lys Tyr Tyr Phe
370 375 380

<210> SEQ ID NO 4
<211> LENGTH: 354
<212> TYPE: PRT
<213> ORGANISM: Bacillus thuringiensis

<400> SEQUENCE: 4

Met Leu Asp Thr Asn Lys Val Tyr Glu Ile Ser Asn His Ala Asn Gly
1 5 10 15

Leu Tyr Ala Ala Thr Tyr Leu Ser Leu Asp Asp Ser Gly Val Ser Leu
20 25 30

Met Asn Lys Asn Asp Asp Asp Ile Asp Asp Tyr Asn Leu Lys Trp Phe
35 40 45

Leu Phe Pro Ile Asp Asp Asp Gln Tyr Ile Ile Thr Ser Tyr Ala Ala
50 55 60

Asn Asn Cys Lys Val Trp Asn Val Asn Asn Asp Lys Ile Asn Val Ser
65 70 75 80

Thr Tyr Ser Ser Thr Asn Ser Ile Gln Lys Trp Gln Ile Lys Ala Asn
85 90 95

Gly Ser Ser Tyr Val Ile Gln Ser Asp Asn Gly Lys Val Leu Thr Ala
100 105 110

Gly Thr Gly Gln Ala Leu Gly Leu Ile Arg Leu Thr Asp Glu Ser Ser
115 120 125

Asn Asn Pro Asn Gln Gln Trp Asn Leu Thr Ser Val Gln Thr Ile Gln
130 135 140

Leu Pro Gln Lys Pro Ile Ile Asp Thr Lys Leu Lys Asp Tyr Pro Lys
145 150 155 160

Tyr Ser Pro Thr Gly Asn Ile Asp Asn Gly Thr Ser Pro Gln Leu Met
165 170 175

Gly Trp Thr Leu Val Pro Cys Ile Met Val Asn Asp Pro Asn Ile Asp
180 185 190

Lys Asn Thr Gln Ile Lys Thr Thr Pro Tyr Tyr Ile Leu Lys Lys Tyr
195 200 205

Gln Tyr Trp Gln Arg Ala Val Gly Ser Asn Val Ala Leu Arg Pro His
210 215 220

Glu Lys Lys Ser Tyr Thr Tyr Glu Trp Gly Thr Glu Ile Asp Gln Lys
225 230 235 240

Thr Thr Ile Ile Asn Thr Leu Gly Phe Gln Ile Asn Ile Asp Ser Gly
245 250 255

Met Lys Phe Asp Ile Pro Glu Val Gly Gly Gly Thr Asp Glu Ile Lys
260 265 270

Thr Gln Leu Asn Glu Glu Leu Lys Ile Glu Tyr Ser His Glu Thr Lys
275 280 285

Ile Met Glu Lys Tyr Gln Glu Gln Ser Glu Ile Asp Asn Pro Thr Asp
290 295 300

Gln Ser Met Asn Ser Ile Gly Phe Leu Thr Ile Thr Ser Leu Glu Leu
305 310 315 320

Tyr Arg Tyr Asn Gly Ser Glu Ile Arg Ile Met Gln Ile Gln Thr Ser
325 330 335

-continued

```
Asp Asn Asp Thr Tyr Asn Val Thr Ser Tyr Pro Asn His Gln Gln Ala
            340                 345                 350

Leu Leu


<210> SEQ ID NO 5
<211> LENGTH: 4
<212> TYPE: PRT
<213> ORGANISM: Bacillus thuringiensis

<400> SEQUENCE: 5

Leu Leu Leu Leu
1


<210> SEQ ID NO 6
<211> LENGTH: 383
<212> TYPE: PRT
<213> ORGANISM: Bacillus thuringiensis

<400> SEQUENCE: 6

Met Leu Asp Thr Asn Lys Ile Tyr Glu Ile Ser Asn Tyr Ala Asn Gly
1               5                   10                  15

Leu His Ala Ala Thr Tyr Leu Ser Leu Asp Asp Ser Gly Val Ser Leu
            20                  25                  30

Met Asn Lys Asn Asp Asp Asp Ile Asp Asp Tyr Asn Leu Arg Trp Phe
        35                  40                  45

Leu Phe Pro Ile Asp Asp Asn Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Ala Ser Ser Tyr Val Ile Gln Ser Asn Asn Gly Lys Val Leu Thr Ala
            100                 105                 110

Gly Thr Gly Gln Ser Leu Gly Leu Ile Arg Leu Thr Asp Glu Ser Pro
        115                 120                 125

Asp Asn Pro Asn Gln Gln Trp Asn Leu Thr Pro Val Gln Thr Ile Gln
    130                 135                 140

Leu Pro Pro Lys Pro Thr Ile Asp Thr Lys Leu Lys Asp Tyr Pro Lys
145                 150                 155                 160

Tyr Ser Gln Thr Gly Asn Ile Asp Lys Gly Thr Pro Pro Gln Leu Met
                165                 170                 175

Gly Trp Thr Leu Ile Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Gln Ala Val Gly Ser Asn Val Ala Leu Arg Pro His
    210                 215                 220

Glu Lys Lys Ser Tyr Ala Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300
```

Gln Ser Met Asn Ser Ile Gly Phe Leu Thr Ile Thr Ser Leu Glu Leu
305 310 315 320

Tyr Arg Tyr Asn Gly Ser Glu Ile Ser Val Met Lys Ile Gln Thr Ser
325 330 335

Asp Asn Asp Thr Tyr Asn Val Thr Ser Tyr Pro Asp His Gln Gln Ala
340 345 350

Leu Leu Leu Leu Thr Asn His Ser Tyr Glu Glu Val Glu Glu Ile Thr
355 360 365

Asn Ile Pro Lys Ile Ser Leu Lys Lys Leu Lys Lys Tyr Tyr Phe
370 375 380

<210> SEQ ID NO 7
<211> LENGTH: 387
<212> TYPE: PRT
<213> ORGANISM: Bacillus thuringiensis

<400> SEQUENCE: 7

Met Ile Glu Thr Asn Lys Ile Tyr Glu Ile Ser Asn Lys Ala Asn Gly
1 5 10 15

Leu Tyr Ala Thr Thr Tyr Leu Ser Phe Asp Asn Ser Gly Val Ser Leu
20 25 30

Leu Asn Lys Asn Glu Ser Asp Ile Asn Asp Tyr Asn Leu Lys Trp Phe
35 40 45

Leu Phe Pro Ile Asp Asn Asn Gln Tyr Ile Ile Thr Ser Tyr Gly Val
50 55 60

Asn Lys Asn Lys Val Trp Thr Ala Asn Gly Asn Lys Ile Asn Val Thr
65 70 75 80

Thr Tyr Ser Ala Glu Asn Ser Ala Gln Gln Trp Gln Ile Arg Asn Ser
85 90 95

Ser Ser Gly Tyr Ile Ile Glu Asn Asn Asn Gly Lys Ile Leu Thr Ala
100 105 110

Gly Thr Gly Gln Ser Leu Gly Leu Leu Tyr Leu Thr Asp Glu Ile Pro
115 120 125

Glu Asp Ser Asn Gln Gln Trp Asn Leu Thr Ser Ile Gln Thr Ile Ser
130 135 140

Leu Pro Ser Gln Pro Ile Ile Asp Thr Thr Leu Val Asp Tyr Pro Lys
145 150 155 160

Tyr Ser Thr Thr Gly Ser Ile Asn Tyr Asn Gly Thr Ala Leu Gln Leu
165 170 175

Met Gly Trp Thr Leu Ile Pro Cys Ile Met Val Tyr Asp Lys Thr Ile
180 185 190

Ala Ser Thr His Thr Gln Ile Thr Thr Thr Pro Tyr Tyr Ile Leu Lys
195 200 205

Lys Tyr Gln Arg Trp Val Leu Ala Thr Gly Ser Gly Leu Ser Val Pro
210 215 220

Ala His Val Lys Ser Thr Phe Glu Tyr Glu Trp Gly Thr Asp Thr Asp
225 230 235 240

Gln Lys Thr Ser Val Ile Asn Thr Leu Gly Phe Gln Ile Asn Thr Asp
245 250 255

Thr Lys Leu Lys Ala Thr Val Pro Glu Val Gly Gly Gly Thr Thr Asp
260 265 270

Ile Arg Thr Gln Ile Thr Glu Glu Leu Lys Val Glu Tyr Ser Ser Glu
275 280 285

Asn Lys Glu Met Arg Lys Tyr Lys Gln Ser Phe Asp Val Asp Asn Leu
290 295 300

-continued

```
Asn Tyr Asp Glu Ala Leu Asn Ala Val Gly Phe Ile Val Glu Thr Ser
305                 310                 315                 320

Phe Glu Leu Tyr Arg Met Asn Gly Asn Val Leu Ile Thr Ser Ile Lys
                325                 330                 335

Thr Thr Asn Lys Asp Thr Tyr Asn Thr Val Thr Tyr Pro Asn His Lys
            340                 345                 350

Glu Val Leu Leu Leu Leu Thr Asn His Ser Tyr Glu Glu Val Thr Ala
        355                 360                 365

Leu Thr Gly Ile Ser Lys Glu Arg Leu Gln Asn Leu Lys Asn Asn Trp
    370                 375                 380

Lys Lys Arg
385
```

TRUNCATED CRY35 PROTEINS

CROSS-REFERENCE TO RELATED APPLICATION

This application claims priority to provisional application Ser. No. 60/584,324, filed Jun. 29, 2004, the disclosure of which is incorporated herein by reference in its entirety.

BACKGROUND OF THE INVENTION

Coleopterans are a significant group of agricultural pests that cause extensive damage to crops each year. Examples of coleopteran pests include corn rootworm and alfalfa weevils. Additional notable examples include Colorado potato beetle, boll weevil, and Japanese beetle.

Insecticidal crystal proteins from some strains of *Bacillus thuringiensis* (B.t.) are well-known in the art. See, e.g., Höfte et al., *Microbial Reviews*, Vol. 53, No. 2, pp. 242-255 (1989). These proteins are typically produced by the bacteria as approximately 130 kDa protoxins that are then cleaved by proteases in the insect midgut, after ingestion by the insect, to yield a roughly 60 kDa core toxin. These proteins are known as crystal proteins because distinct crystalline inclusions can be observed with spores in some strains of B.t. These crystalline inclusions often comprise a mixture of distinct proteins.

An entirely new insecticidal protein system was discovered in *Bacillus thuringiensis* as disclosed in WO 97/40162. Unlike the 130 kDa-type protoxins, this new system comprises two proteins—one of approximately 15 kDa and the other of about 45 kDa. See also U.S. Pat. No. 6,083,499; U.S. Pat. No. 6,127,180; Moellenbeck et al., *Nature Biotechnology* 19:668-672 (2001); and Ellis et al., *Applied and Environmental Microbiology* 68:1137-1145 (2002). These proteins have now been assigned to their own classes, and accordingly received the Cry designations of Cry34 and Cry35, respectively. See Crickmore et al. website (biols.susx.ac.uk/home/Neil_Crickmore/Bt/). Many other proteins of this type of system have now been disclosed. See e.g. U.S. Pat. No. 6,372,480; WO 01/14417; and WO 00/66742. Plant-optimized genes that encode such proteins, wherein the genes are engineered to use codons for optimized expression in plants, have also been disclosed. See e.g. U.S. Pat. No. 6,218,188 and WO 00/24904.

BRIEF SUMMARY OF THE INVENTION

This invention provides truncated Cry35 proteins that surprisingly and unexpectedly have increased pesticidal activity as compared to full-length Cry35 proteins. The subject invention also includes polynucleotides that encode these truncated proteins, transgenic plants comprising a truncated gene of the subject invention, and transgenic plants that produce these truncated proteins. This invention further provides methods of controlling plant pests, including rootworms, with these truncated proteins. The truncated Cry35 proteins of the subject invention are preferably used in combination with Cry34 proteins, which are known in the art. Various surprising advantages of the subject invention will be apparent in light of this disclosure.

BRIEF DESCRIPTION OF THE FIGURES

FIG. 1 shows a sequence alignment of Cry35Aa1 (80JJ1), Cry35Ab1 (149B1), Cry35Ac1 (167H2), and 201L3 (~45 kDa). The truncation site is in the middle of the 4-leucine (L) run towards the C terminus. The amino acid sequence to be removed starts at and includes the third and fourth "Ls" to the C terminus.

BRIEF DESCRIPTION OF THE SEQUENCES

SEQ ID NO:1 is the amino acid sequence of the wild-type 80JJ1 ~45 kDa (Cry 35Aa1) protein.

SEQ ID NO:2 is the amino acid sequence of a preferred, truncated 80JJ1 ~40 kDa (Cry 35Aa1) protein that exhibits enhanced toxin activity.

SEQ ID NO:3 is the amino acid sequence of the wild-type 149B1 ~45 kDa (Cry 35Ab1) protein.

SEQ ID NO:4 is the amino acid sequence of a preferred, truncated 149B1 ~40 kDa (Cry 35Ab1) protein.

SEQ ID NO:5 is the 4-leucine (L) run towards the C terminus, the middle of which is the truncation site.

SEQ ID NO:6 is the amino acid sequence of Cry35Ac1 (167H2) (GenBank Accession No. AAG50117) disclosed as SEQ ID NO:38 in WO 01/14417.

SEQ ID NO:7 is the amino acid sequence of 201L3 (~45 kDa) disclosed as SEQ ID NO:136 in WO 01/14417.

DETAILED DESCRIPTION

This invention provides truncated Cry35 proteins that surprisingly and unexpectedly have increased pesticidal activity as compared to full-length Cry35 proteins. Preferred proteins of the subject invention are approximately 40 kDa. Wild-type Cry35 proteins are typically about 45 kDa.

The subject invention also includes polynucleotides that encode these truncated proteins, transgenic plants comprising a truncated gene of the subject invention, and transgenic plants that produce these truncated proteins. Seeds and other materials (such as pollen and germ plasm) produced by such plants are also included within the subject invention. This invention further provides methods of controlling plant pests, including rootworms, by contacting the pests with these truncated proteins. The truncated Cry35 proteins of the subject invention are preferably used in combination with Cry34 proteins, which are known in the art. Various surprising advantages of the subject invention will be apparent in light of this disclosure.

While some B.t. proteins are known to undergo protealytic processing in vivo, there was no reason to expect the subject truncations to have better activity than the wild-type form. Thus, there was no prior motivation or suggestion to use the subject truncated genes in plants. Likewise there was no motivation or suggestion to provide (i.e., directly administer) a truncated Cry35 protein to a pest so that the pest would ingest/consume the truncated protein.

Polynucleotides of the subject invention preferably have codon usage that is optimized for expression in plants. Various techniques for doing so are well-known in the art.

The subject invention includes methods of controlling and/or inhibiting pests, preferably a rootworm pest, wherein the methods includes contacting the pest with a protein of the subject invention. Preferably, the truncated protein of the subject invention is produced by and is present in a transgenic plant comprising a gene that encodes the truncated protein. By consuming material of this transgenic plant, such as root cells of such plant, the pest thereby contacts the subject proteins, which is preferably in the plant cells consumed by the pest.

Proteins of the subject invention having "toxin activity," as the term is used herein, include proteins that enhance or improve the activity of other toxin proteins. Cry35 proteins are known to act with Cry34 proteins to exert the toxic effects. There are some reports that Cry34 proteins can be toxic alone, but that toxicity is much improved when used with Cry35 proteins. The subject invention provides a very surprising means for still further increasing the Cry34/35 activity.

When an insect comes into contact with an effective amount of a "toxin" of the subject invention delivered via transgenic plant expression, formulated protein composition (s), sprayable protein composition(s), a bait matrix or other delivery system, the results are typically death of the insect, inhibition of the growth and/or proliferation of the insect, and/or prevention of the insects from feeding upon the source (preferably a transgenic plant) that makes the toxins available to the insects. Complete lethality to feeding insects is preferred, but is not required to achieve toxin activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage. Insects inhibited by the methods and proteins of the subject invention include those that are killed by the subject methods and proteins.

Without being bound by any specific theory of a mechanism of action, and noting that the following theory is now possible in light of the subject disclosure, the removal of the C terminus could facilitate assembly of truncated Cry35 proteins into a multimer (comprised of truncated, Cry35 monomers). There are other proteins having a motif where an activation domain is protealytically removed to allow assembly of multimers. Noting that the Cry35 protein is known to act with the Cry34 (~14 kDa) protein, the Cry34 protein could bind to the multimeric form of assembled Cry35 proteins. This could facilitate entry of the 14 kDa protein, which may have a cellular target via binding, or may form pores on its own. It appears unlikely that a membrane-bound Cry35 monomer associates with the membrane and then with the 14 kDa as a binding partner.

While the 149B1 protein is specifically exemplified, any other cry35 gene or protein can be used according to the subject invention, as Cry35 proteins have similar structures and features. Thus, as one skilled in the art would know, with the benefit of this disclosure, corresponding residues and segments are now identifiable in the other Cry35 proteins. Thus, the specific examples disclosed herein can be applied to the other proteins in the Cry35 family. The exact numbering of the residues might not strictly correspond to the 149B1 protein, but the corresponding residues are readily identifiable in light of the subject disclosure. In this regard, some sequences of various Cry35 proteins and genes described in various patent references are indicated below (such sequences can be used according to some embodiments of the subject invention):

| Cry designation | Source isolate | GENBANK Acc. No. |
|---|---|---|
| 35Aa1 | PS80JJ1 | AAG50342 |
| 35Aa2 | EG5899 | AAK64561 |
| 35Ab1 | PS149B1 | AAG41672 |
| 35Ab2 | EG9444 | AAK64563 |
| 35Ac1 | PS167H2 | AAG50117 |
| 35Ba1 | EG4851 | AAK64566 |

35Aa1, 35Ab1, and 35Ac1 are also disclosed in WO 01/14417 as follows. The location (amino acid residue numbers) of the four leucine run (LLLL) (SEO ID NO:5) is also indicated.

| Source isolate | SEQ ID NO: IN WO 01/14417 | Length | Location of LLLL (SEQ ID NO:5) |
|---|---|---|---|
| PS80JJ1 | 11 | 385 | 353-356 |
| PS167H2 | 38 | 383 | 353-356 |
| PS149B1 | 43 | 383 | 353-356 |

There are many additional Cry35 sequences disclosed in WO 01/14417 that can be used according to the subject invention. For example:

| Source isolate | SEQ ID NO: IN WO 01/14417 | Location of LLLL (SEQ ID NO:5) |
|---|---|---|
| PS131W2 | 54 | 353-356 |
| PS158T3 | 58 | 353-356 |
| PS185FF | 64 | 353-356 |
| PS185GG | 68 | 353-356 |
| PS187F3 | 78 | 353-356 |
| PS187L14 | 86 | 353-356 |
| PS187Y2 | 90 | 340-344 |
| PS69Q | 116 | 353-356 |
| KR589 | 126 | 353-356 |
| PS201L3 | 136 | 355-358 |
| PS187G1 | 140 | 353-356 |
| PS201HH2 | 144 | (partial sequence) |
| KR1369 | 148 | 353-356 |

Several other source isolates are also disclosed in WO 01/14417. The PS designation of the source isolate can be dropped for ease of reference when referring to a protein obtainable from that isolate. For example, it can be noted that the full-length 201L3 Cry35 protein is 387 residues long. Polynucleotides that encode various Cry35 proteins are also disclosed in various references cited herein and are known in the art.

As shown by the above tables, the typical and preferred site for truncation is after residue 354 for most Cry35 proteins. Thus, preferred truncated Cry35 proteins consist of 354 amino acid residues. Accordingly, in preferred embodiments, approximately 29 residues are removed from the C terminus of the wild-type/full-length Cry35 protein. However, approximately 31 residues (in the case of 80JJ1, for example) or 33 residues (in the case of 201L3, for example) can be removed from the C terminus. Some preferred proteins of the subject invention can be 356 amino acid residues in length (in the case of 201L3, for example).

With that noted, truncated Cry35 proteins of the subject invention can be part of a larger fusion protein. For example, an approximately 354-residue, truncated Cry35 protein can be fused to a Cry34 protein to make a Cry35/Cry34 chimeric protein. Thus, such proteins can be said to comprise approximately 354 (or 356) Cry35 residues. A Cry35/Cry34 fusion is disclosed in WO 01/14417 as SEQ ID NO:159, with LLLL (SEQ ID NO:5) occurring at residue positions 353-356.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes that encode activated fragments of the subject invention can be obtained using a variety of restriction enzymes. Proteases may be used to directly obtain activated fragments of the subject invention.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art.

As used herein, reference to "isolated" and/or "purified" proteins and/or polynucleotides indicates that such molecules are not in their native state. Thus, reference to "isolated" and/or "purified" signifies the involvement of the "hand of man" as described herein. For example, a bacterial toxin "gene" of the subject invention put into a plant for expression is an "isolated polynucleotide." Likewise, a protein of the subject invention that is produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, toxins. These variant DNA sequences are within the scope of the subject invention.

Certain toxins of the subject invention have been specifically exemplified herein. As these toxins are merely exemplary of the proteins of the subject invention, it should be readily apparent that the subject invention comprises variant or equivalent proteins (and nucleotide sequences coding for equivalents thereof) having the same (or similar), increased toxin activity of the exemplified proteins. Genes and toxins of the subject invention include not only the specifically exemplified sequences, but also variants, mutants, chimerics, and fusions thereof. Proteins of the subject invention can have substituted amino acids so long as they retain the approximate size and the increased toxin activity of the truncated proteins exemplified herein. As used herein, reference to a "variant" or an "equivalent" sequence refers to sequences having amino acid substitutions, deletions, additions, as compared to the wild-type sequence corresponding to a truncation of the subject invention, so long as the increased toxin activity exhibited by the truncated protein is retained. Thus, truncated proteins of the subject invention include not only those having a wild-type sequence that is truncated. Some residues can be substituted. While conservative changes are preferred, nonconservative changes can also be made in some cases. Techniques for producing and confirming the activity of proteins modified accordingly are well-known in the art.

Equivalent toxins and/or genes encoding these equivalent toxins can be obtained/derived from wild-type or recombinant bacteria and/or from other wild-type or recombinant organisms using the teachings provided herein. Other *Bacillus* and *Paenibacillus* species, for example, can be used as source isolates.

Variations of genes may be readily constructed using standard techniques for making point mutations, for example. In addition, U.S. Pat. No. 5,605,793, for example, describes methods for generating additional molecular diversity by using DNA reassembly after random fragmentation. Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, or 357 contiguous residues (amino acid or nucleotide) of any of the exemplified or suggested sequences (or the complements (full complements) thereof). Full-length genes obtained by shuffling can then be truncated according to the subject invention (or truncated genes can be subjected to shuffling).

Variant/equivalent, truncated (and activated) toxins included within the scope of the subject invention will be of a length suggested herein and will have some level of amino acid identity, similarity, and/or homology with an exemplified activated toxin. This degree of amino acid identity with an exemplified, truncated toxin is preferably greater than 60%, preferably greater than 75%, more preferably greater than 80%, even more preferably greater than 90%, and can be greater than 95%. Preferred polynucleotides and proteins of the subject invention can also be defined in terms of more particular identity and/or similarity ranges. For example, this identity and/or similarity can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified or suggested herein.

Unless otherwise specified, as used herein, percent sequence identity and/or similarity of two sequences is determined using the algorithm of Karlin and Altschul (1990), *Proc. Natl. Acad. Sci. USA* 87:2264-2268, modified as in Karlin and Altschul (1993), *Proc. Natl. Acad. Sci. USA* 90:5873-5877. Such an algorithm is incorporated into the NBLAST and XBLAST programs of Altschul et al. (1990), *J. Mol. Biol.* 215:402-410. BLAST nucleotide searches are performed with the NBLAST program, score=100, wordlength=12. To obtain gapped alignments for comparison purposes, Gapped BLAST is used as described in Altschul et al. (1997), *Nucl. Acids Res.* 25:3389-3402. When utilizing BLAST and Gapped BLAST programs, the default parameters of the respective programs (NBLAST and XBLAST) are used. See NCBI/NIH website. The scores can also be calculated using the methods and algorithms of Crickmore et al. as described in the Background section, above.

The amino acid homology/similarity/identity can be highest in critical regions of the protein that account for its toxin activity or that are involved in the determination of three-dimensional configurations that are ultimately responsible for the toxin activity. In this regard, certain amino acid substitutions are acceptable and can be tolerated. For example, these substitutions can be in regions of the protein that are not critical to activity. Analyzing the crystal structure of a protein, and software-based protein structure modeling, can be used to identify regions of a protein that can be modified (using site-directed mutagenesis, shuffling, etc.) to actually change the properties and/or increase the functionality of the protein.

In many cases, conservative amino acid substitutions can be made. Unless otherwise specified, amino acids can be placed in the following classes: non-polar, uncharged polar, basic, and acidic. Conservative substitutions whereby an amino acid of one class is replaced with another amino acid of the same type are within the scope of the subject invention so long as the substitution is not adverse to the elevated toxin activity exhibited by truncated proteins of the subject invention. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the functional/biological/toxin activity of the protein.

In other embodiments, polynucleotides (and the proteins they encode) of the subject invention can be defined by their ability to hybridize with exemplified and/or suggested polynucleotides. The nucleotide sequences of the subject invention are particularly advantageous, and they encode proteins that are distinct from previously described proteins. Thus, exemplified or suggested polynucleotides (and/or the complements thereof) can be used as hybridization probes.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA are included in the subject invention.

Polynucleotides of the subject invention, when accordingly used as probes to define other polynucleotides (or proteins) that are within the scope of the subject invention, can be made detectable by virtue of an appropriate label or may be made inherently fluorescent as described in International Application No. WO 93/16094. The probes/polynucleotides of the subject invention may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes). Thus, where a synthetic, degenerate oligonucleotide is referred to herein, and "N" or "n" is used generically, "N" or "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted, followed by washes under conditions of low, moderate, or high stringency by techniques well-known in the art, as described in, for example, Keller, G. H., M. M. Manak (1987) *DNA Probes*, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1×SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water, adjusting pH to 7.0 with 10 N NaOH, then adjusting the volume to 1 liter 10% SDS can be prepared by dissolving 10 g of SDS in 50 ml of autoclaved water, then diluting to 100 ml.

Detection of the probe provides a means for determining in a known manner whether hybridization has been maintained. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein. That is, one way to define a truncated gene of the subject invention is by the size of the protein it encodes (i.e., the protein or polypeptide segment will be of a length disclosed or suggested herein) and by its ability to hybridize (under any of the conditions specifically disclosed herein) with an exemplified or suggested sequence, such as a polynucleotide encoding a truncated protein of SEQ ID NO:2 and/or SEQ ID NO:4, for example. The same is true for a polynucleotide encoding a truncated 158×10 Cry35 protein, for example, of the subject invention.

As used herein, "stringent" conditions for hybridization refers to conditions which achieve the same, or about the same, degree of specificity of hybridization as the conditions employed by the current applicants. Specifically, hybridization of immobilized DNA on Southern blots with $^{32}P$-labeled gene-specific probes was performed by standard methods (see, e.g., Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under conditions that allowed for detection of target sequences. For double-stranded DNA gene probes, hybridization was carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266-285):

$$Tm=81.5° \text{ C.}+16.6 \text{ Log [Na+]}+0.41(\% \ G+C)-0.61(\% \text{ formamide})-600/\text{length of duplex in base pairs.}$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

$$Tm(° \text{ C.})=2(\text{number } T/A \text{ base pairs})+4(\text{number } G/C \text{ base pairs})$$

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683-693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

All patents, patent applications, provisional applications, and publications referred to or cited herein are incorporated by reference in their entirety to the extent they are not inconsistent with the explicit teachings of this specification.

Following is an example that illustrates procedures for practicing the invention. These examples should not be construed as limiting. All percentages are by weight and all solvent mixture proportions are by volume unless otherwise noted.

EXAMPLE

Improved Efficacy of Truncated Cry35Ab1

The native intact Cry35Ab1 protein from B.t. PS149B1 is approximately 44 kDa. This 44-kDa protein (intact or full-length form), when expressed in the bacteria and transgenic plants, is susceptible to cleavage by proteases producing a stable truncated form. The truncated Cry35Ab1 has a molecular weight of 40.3-kDa determined by matrix-assisted laser desorption/ionization time-of-flight mass spectrometry (MALDI-TOF MS). It was determined that both the intact and truncated forms possess the same N-terminal sequence, indicating that the truncation occurred at the C-terminal domain. The results of the molecular mass determined by MALDI-TOF MS, together with data of N-terminal sequencing, suggest that the 40.3-kDa truncated Cry35Ab1 protein contains amino acids residues of 1-354 of the intact Cry35Ab1, i.e., the cleavage site is between amino acid residue #354 and #355 ($L^{353}L^{354}\downarrow L^{355}L^{356}$) (SEQ ID NO:5). This cleavage site was further confirmed by the data of C-terminal sequence obtained with PSD (post source decay) mode of MALDI-TOF MS and carboxypeptidase digestion techniques.

As displayed in FIG. 1, the sequence segment of the 4 L (leucine) is quite conserved among the Cry35 protein family. This cleavage site appears to be universal to the whole family of Cry35 proteins.

The truncated version of the Cry35Ab1 protein was found to be more efficacious than the non-truncated version in terms of synergizing the Cry34Ab1 protein. This same efficacy improvement can be effected in transgenic plants and with homologous proteins.

Ten diet-overlay assays were conducted against neonate southern corn rootworm, *Diabrotica undecimpuctata howardi*. Purified full-length and truncated Cry35Ab1 proteins were each applied at 0.5 μg/cm$^2$ in combination with Cry34Ab1 at 0.5 μg/cm$^2$. Controls consisted of Cry34Ab1 alone applied at 0.5 μg/cm$^2$, and a buffer blank. Sixteen insects were included for each treatment for each of ten bioassays. Insect weights were collected for each group of 16 insects in each bioassay after six days of exposure to the treated diet. Statistical analysis consisted of ANOVA analysis of logarithmically transformed insect weights followed by mean comparisons using Duncan's Multiple Range Test. The logarithmic transformation was used to improve the homogeneity of variance. A second ANOVA of the raw weights was also carried out for the two Cry35Ab1 treatments alone where good homogeneity of variance was seen. Mean insect weights for the buffer control, Cry34Ab1 alone, full-length Cry35Ab1+Cry34Ab1, and truncated Cry35Ab1+Cry34Ab1 treatments were 15.7, 11.9, 8.8, and 6.9 mg/16 insects, respectively. Significant differences in insect weight were seen between all treatments. The concentrations of the mixtures were based on a model generated using a preparation of Cry35Ab1 that contained a mixture of full-length and truncated protein (Herman, R. A., Scherer, P. N., Young, D. L., Mihaliak, C. A., Meade, T., Woodsworth, A. T., Stockhoff, B. A., and Narva, K. E., 2002, "Binary Insecticidal Crystal Protein from *Bacillus thuringiensis* strain PS149B1: effects of individual protein components and mixtures in laboratory bioassays," *J. Econ. Entomol.* 95:635-639). This model predicts 50% growth inhibition (GI) at the tested concentrations. The full-length protein mixture in the tests reported here averaged 44% GI, while the truncated protein mixture averaged 56% GI. This improvement in GI translates to a ten-fold improvement in potency based on the model described in Herman et al. (2002). This analysis thus demonstrates an improvement in the activity of the truncated Cry35Ab1 protein compared to the full-length form.

We claim:

1. A polynucleotide that encodes an isolated, truncated Cry35 protein having a truncated C terminus and improved toxin enhancing activity against an insect, as compared to a full-length Cry35 molecule, wherein said protein enhances toxin activity of a Cry34 molecule, said protein has 354 amino acid residues, said protein has leucine-leucine residues as its C-terminal amino acids, and said protein has at least 95% sequence identity with an amino acid sequence selected from the group consisting of SEQ ID NO:2 and SEQ ID NO:4.

2. The polynucleotide of claim 1, wherein said protein has a molecular weight of approximately 40 kDa and said Cry35 molecule has a molecular weight of approximately 45 kDa.

3. The polynucleotide of claim 1, wherein said protein is fused to a Cry34 polypeptide.

4. A polynucleotide that encodes a protein that consists essentially of an amino acid sequence selected from the group consisting of SEQ ID NO:2 and SEQ ID NO:4.

5. The polynucleotide of claim 1, wherein any amino acid changes are conservative substitutions.

6. The polynucleotide of claim 1, wherein said insect is a corn rootworm.

7. The polynucleotide of claim 1, wherein said polynucleotide has a codon composition that is optimized for expression in plants.

8. A plant comprising the polynucleotide of claim 1.

9. A transgenic plant cell or bacterial cell comprising the polynucleotide of claim 1.

10. A method of inhibiting a rootworm wherein said method comprises providing a Cry34 protein and a truncated Cry35 protein encoded by the polynucleotide of claim 1 to said rootworm for ingestion, wherein said Cry34 protein and said truncated Cry35 protein are produced by and are present in a plant.

11. A plant expression vector comprising the polynucleotide of claim 1.

* * * * *